US010557817B2

(12) United States Patent
Okamoto et al.

(10) Patent No.: US 10,557,817 B2
(45) Date of Patent: Feb. 11, 2020

(54) METHOD OF INSPECTING ELECTRODE PROVIDED IN GAS SENSOR ELEMENT

(71) Applicant: NGK INSULATORS, LTD., Nagoya-shi, Aichi (JP)

(72) Inventors: Taku Okamoto, Nagoya (JP); Yuki Nakayama, Nagoya (JP); Soichiro Yoshida, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 60 days.

(21) Appl. No.: 15/996,560

(22) Filed: Jun. 4, 2018

(65) Prior Publication Data

US 2018/0356364 A1 Dec. 13, 2018

(30) Foreign Application Priority Data

Jun. 12, 2017 (JP) ................................ 2017-115093

(51) Int. Cl.
*G01R 27/08* (2006.01)
*G01N 27/416* (2006.01)
(Continued)

(52) U.S. Cl.
CPC ....... *G01N 27/4163* (2013.01); *G01N 27/041* (2013.01); *H01L 22/34* (2013.01); *G01D 5/06* (2013.01); *G01D 5/165* (2013.01); *G01D 5/2417* (2013.01); *G01D 11/245* (2013.01); *G01N 27/4067* (2013.01); *G01N 27/4071* (2013.01); *G01N 27/4076* (2013.01);
(Continued)

(58) Field of Classification Search
CPC ......... H01L 2924/0002; H01L 2924/00; H01L 22/34; H01L 2224/131; G01D 5/165; G01D 5/06; G01D 5/2417; G01D 11/245
USPC .......... 324/76.11–76.83, 459, 600, 635, 644, 324/649, 662, 671, 691, 693, 699, 716
See application file for complete search history.

(56) References Cited

U.S. PATENT DOCUMENTS

2011/0138875 A1* 6/2011 Shindo ............... G01N 27/4071 73/23.31
2013/0255352 A1* 10/2013 Ohtsubo ............... G01R 31/28 73/1.06

(Continued)

FOREIGN PATENT DOCUMENTS

JP 2016-33510 A 3/2016
JP 5918434 B1 5/2016

*Primary Examiner* — Raul J Rios Russo
(74) *Attorney, Agent, or Firm* — Mattingly & Malur, PC

(57) ABSTRACT

A method of inspecting an electrode provided in a gas sensor element includes the steps of: producing, in advance, a calibration curve representing a relation between an Au maldistribution degree defined based on a ratio of an area of a portion at which Au is exposed on a noble metal particle surface and calculated from a result of XPS or AES analysis on an inspection target electrode, and a predetermined alternative maldistribution degree index correlated with the Au maldistribution degree and acquired in a non-destructive manner from the gas sensor element heated to a predetermined temperature; acquiring a value of the alternative maldistribution degree index for the inspection target electrode of the gas sensor element while the gas sensor element is heated to the predetermined temperature; and determining whether the Au maldistribution degree satisfies a predetermined standard based on the calibration curve and the acquired inspection value.

20 Claims, 9 Drawing Sheets

101A A 20 10 30 100A 50 Sa 6 5 75 40 4 3 E1 E2 2 Sb 1 74 72 A' 70 73 71

(51) Int. Cl.

| | |
|---|---|
| ***H01L 21/66*** | (2006.01) |
| ***G01N 27/04*** | (2006.01) |
| *G01D 5/06* | (2006.01) |
| *G01D 5/241* | (2006.01) |
| *G01D 11/24* | (2006.01) |
| *G01D 5/165* | (2006.01) |
| *G01N 27/406* | (2006.01) |
| *G01N 27/407* | (2006.01) |

(52) U.S. Cl.
CPC .... *H01L 2224/131* (2013.01); *H01L 2924/00* (2013.01); *H01L 2924/0002* (2013.01)

(56) References Cited

U.S. PATENT DOCUMENTS

2016/0033447 A1 2/2016 Nakasone et al.
2017/0184538 A1 6/2017 Okamoto et al.
2017/0284960 A1* 10/2017 Takegawa .......... G01N 27/4074

* cited by examiner

F I G. 2
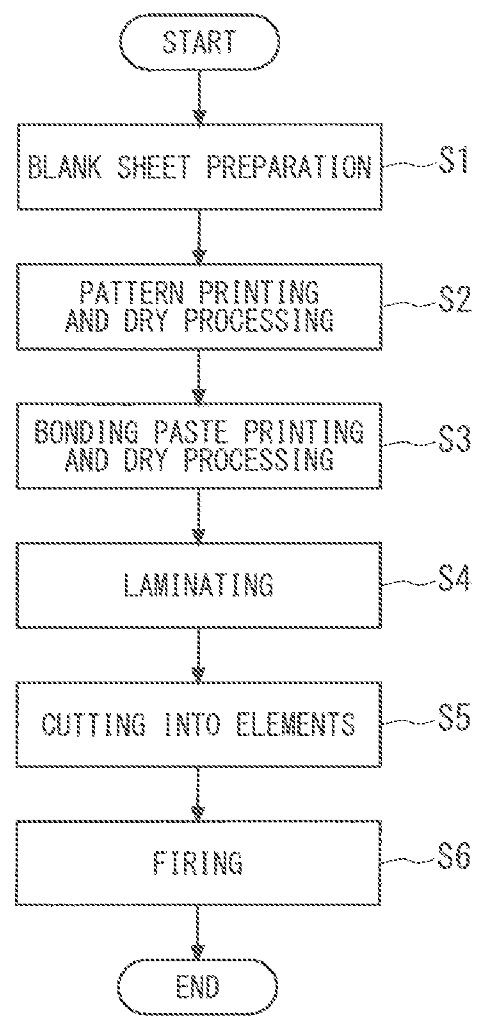

F I G. 4
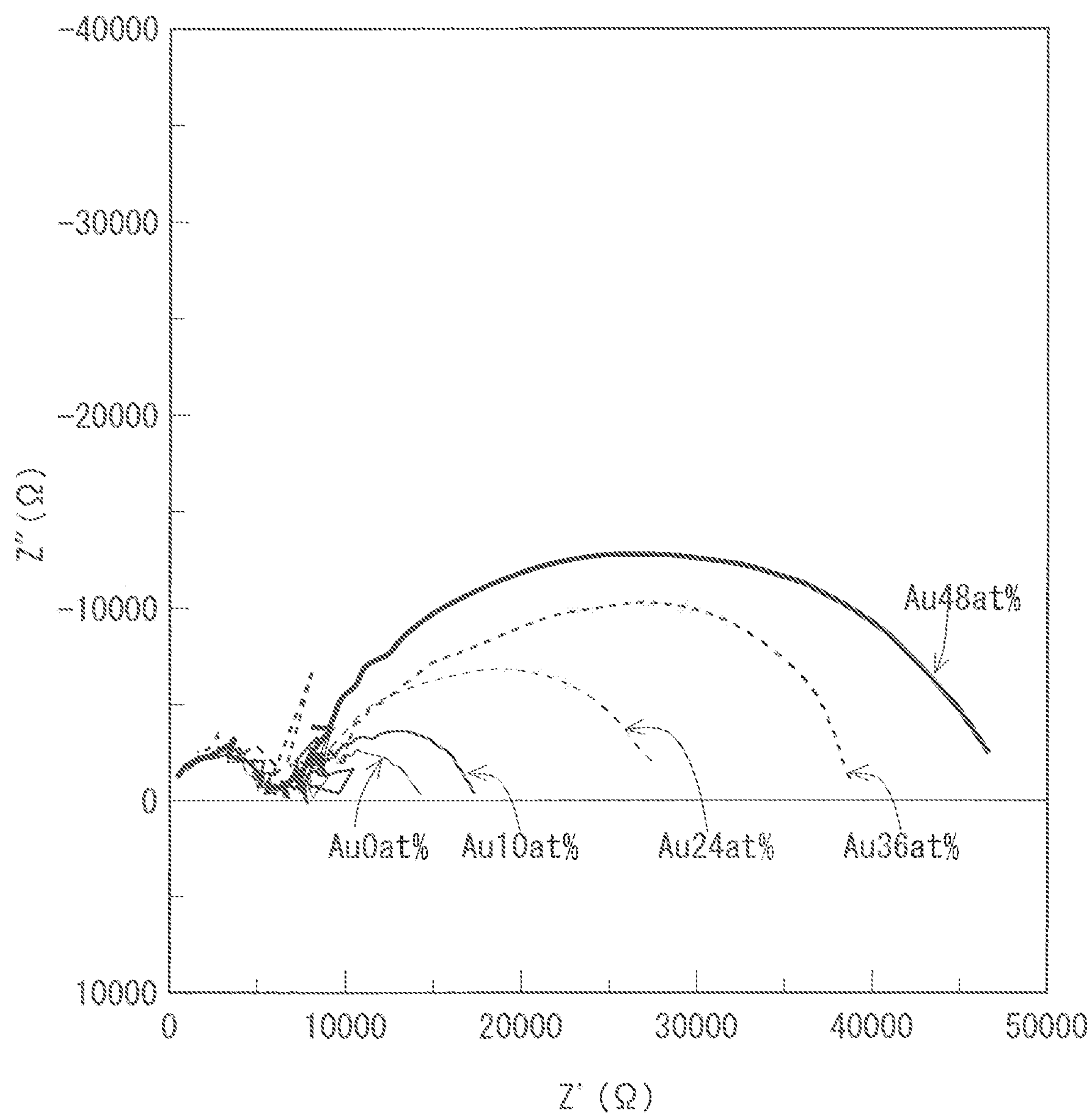

F I G . 7
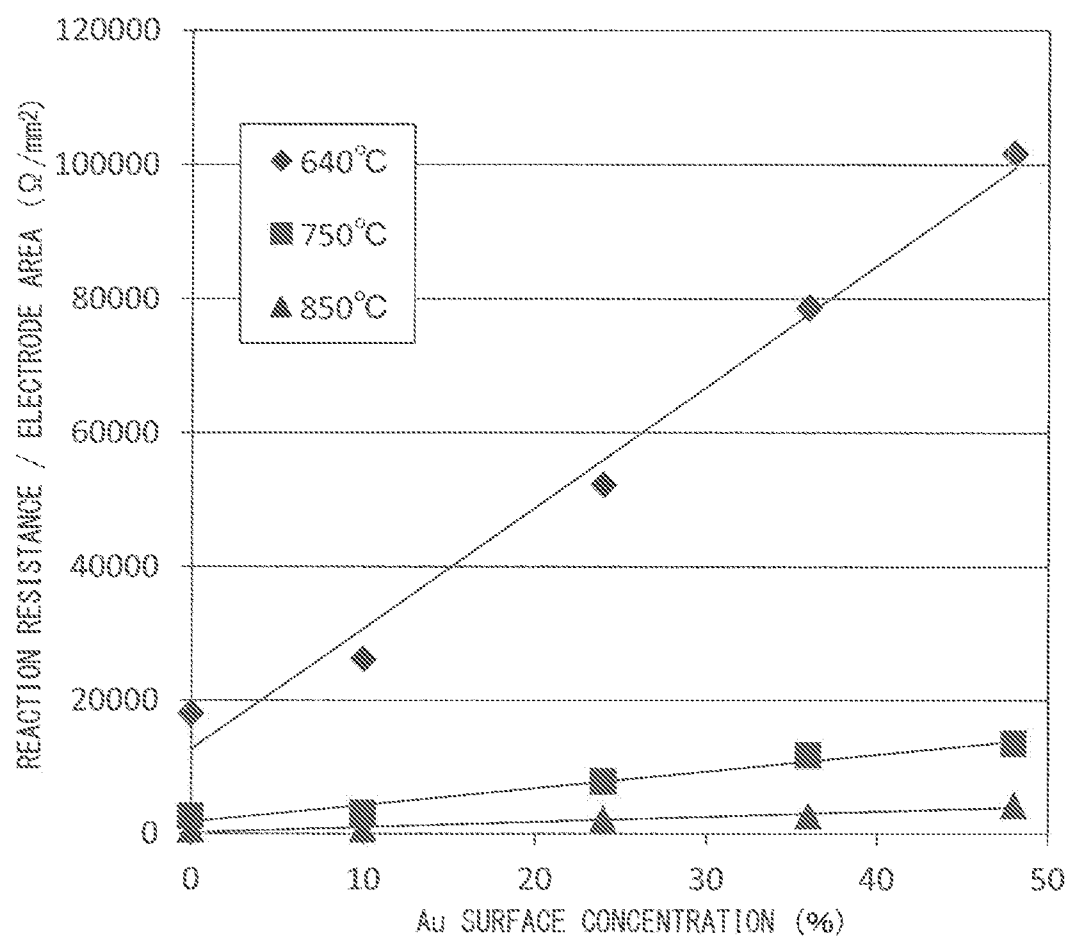

F I G. 9
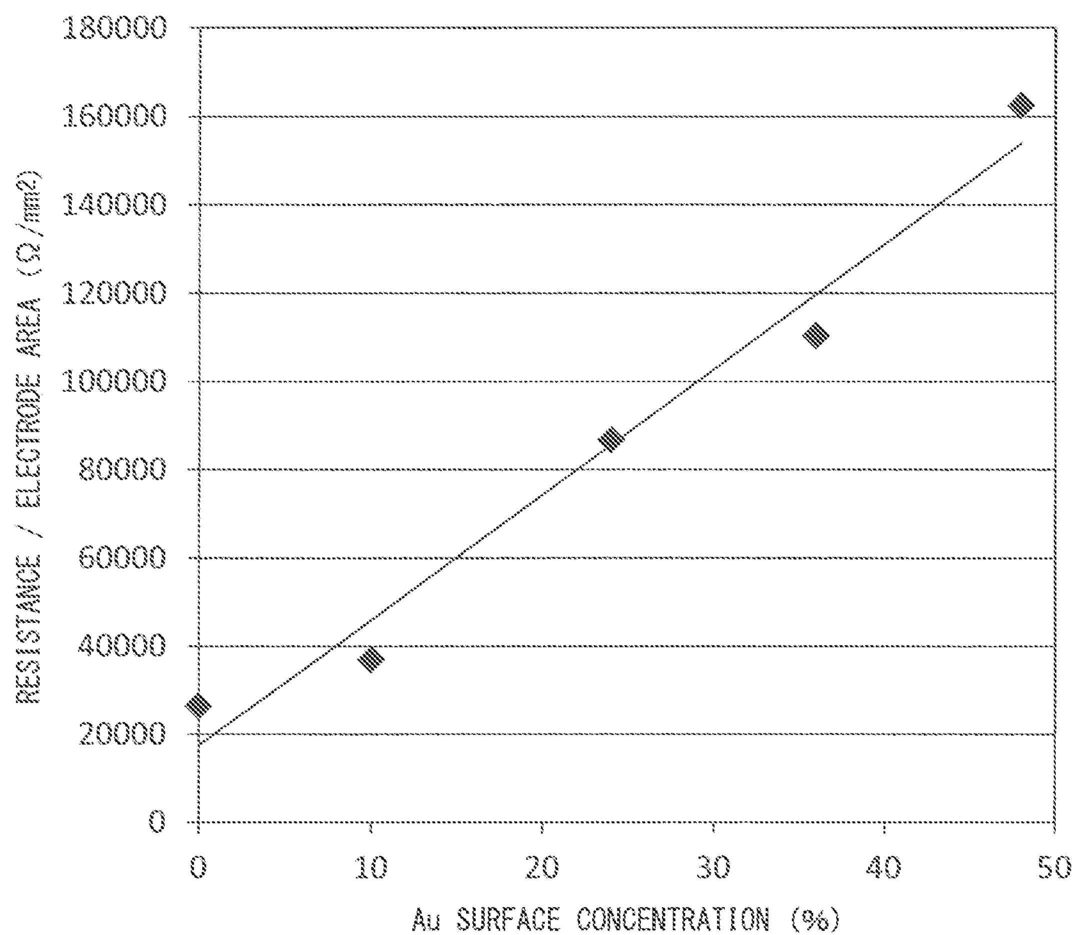

METHOD OF INSPECTING ELECTRODE PROVIDED IN GAS SENSOR ELEMENT

CROSS-REFERENCE TO RELATED APPLICATION

The present application claims priority from Japanese application JP 2017-115093, filed on Jun. 12, 2017, the content of which is hereby incorporated by reference into this application.

BACKGROUND OF THE INVENTION

Field of the Invention

The present invention relates to a method of inspecting an electrode provided in a gas sensor element, and particularly relates to non-destructive inspection of an Au maldistribution degree.

Description of the Background Art

Gas sensors configured to sense a predetermined gas component in measurement gas to determine the concentration thereof come in various types such as a semiconductor type, a catalytic combustion type, an oxygen-concentration difference sensing type, a limiting current type, and a mixed-potential type. Some of these gas sensors include a sensor element mainly made of ceramic which is solid electrolyte such as zirconia.

Such gas sensors include publicly known mixed-potential gas sensors whose sensing target components is hydrocarbon gas or ammonia gas, having a sensing electrode made of a cermet of noble metals (specifically, Pt and Au) and oxygen-ion conductive solid electrolyte on a surface of the sensor element, and ensuring a sufficient detection sensitivity by maldistribution of Au on the surface of a noble metal particle forming the sensing electrode (by increasing the Au abundance ratio at the surface of a noble metal particle) (refer to Japanese Patent Application Laid-Open No. 2016-33510 and Japanese Patent No. 5918434, for example).

In aspects disclosed in Japanese Patent Application Laid-Open No. 2016-33510 and Japanese Patent No. 5918434, the Au abundance ratio at the surface of the sensing electrode provided in the sensor element means the area ratio of a portion covered by Au to a portion at which Pt is exposed on the surface of a noble metal particle forming the sensing electrode, and the Au abundance ratio is evaluated based on a result of X-ray photoelectron spectroscopy (XPS) analysis or Auger electron spectroscopy (AES) analysis on the sensing electrode.

In this case, the sensing electrode, which is covered by a surface protective layer, needs to be exposed to perform the evaluation of the Au abundance ratio at the sensing electrode. This exposure can be achieved by, for example, peeling the surface protective layer or breaking the sensor element at the position of the sensing electrode to analyze the broken-out section of the sensing electrode. However, when the sensing electrode has a small film thickness or a small electrode area, it is difficult to desirably exposure the sensing electrode for analysis in some cases.

As a matter of course, evaluation of the Au abundance ratio by peeling the surface protective layer or breaking the sensor element cannot be used in one-hundred percent inspection in mass production of the sensor elements.

SUMMARY

The present invention relates to a method of inspecting an electrode provided in a gas sensor element, and is particularly directed to non-destructive inspection of an Au maldistribution degree on a noble metal particle surface of the electrode.

According to the present invention, a method of inspecting an Au maldistribution degree at a noble metal particle surface of an inspection target electrode, when the inspection target electrode is provided in a gas sensor element made of oxygen-ion conductive solid electrolyte, and the inspection target electrode contains Pt and Au as noble metal components, and the gas sensor element includes a heater inside, the method includes the steps of: a) producing, in advance, a calibration curve representing a relation between the Au maldistribution degree and a predetermined alternative maldistribution degree index correlated with the Au maldistribution degree and acquired in a non-destructive manner from the gas sensor element heated to a predetermined temperature by the heater; b) acquiring, as an inspection value, a value of the alternative maldistribution degree index for the inspection target electrode of the gas sensor element as an inspection target while the gas sensor element is heated to the predetermined temperature; and c) determining whether the Au maldistribution degree at the inspection target electrode satisfies a predetermined standard based on the calibration curve produced through the step a) and the inspection value acquired through the step b).

According to the present invention, the Au maldistribution degree at an inspection target electrode can be inspected without destructing a sensor element and faster than a case in which XPS analysis or AES analysis is performed.

Preferably, the alternative maldistribution degree index is preferably a value of direct-current resistance between the inspection target electrode and the reference electrode or a value of direct current flowing between the inspection target electrode and the reference electrode when predetermined direct-current voltage is applied between the inspection target electrode and a predetermined reference electrode provided in the gas sensor element.

With this configuration, the Au maldistribution degree at the inspection target electrode can be inspected faster than a case in which complex impedance measurement is performed.

The present invention is intended to provide a method capable of inspecting, by a simple method, the Au maldistribution degree on a noble metal particle surface of a sensing electrode provided in a sensor element of a gas sensor.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a diagram illustrating the flow of processing of manufacturing a sensor element 101A;

FIG. 4 is a Nyquist diagram illustrating a result of two-terminal complex impedance measurement performed at a sensor drive temperature of 640° C. to obtain the reaction resistances of five sensor elements 101A having different Au maldistribution degrees at a sensing electrode 10;

FIG. 7 is a diagram plotting a reaction resistance value per unit area of the sensing electrode 10 against an Au surface concentration;

FIG. 9 is a diagram plotting the direct-current resistance value per unit area of the sensing electrode 10 against the Au surface concentration.

DESCRIPTION OF THE PREFERRED EMBODIMENTS

<Exemplary Configuration of Gas Sensor>

Figure 1A:
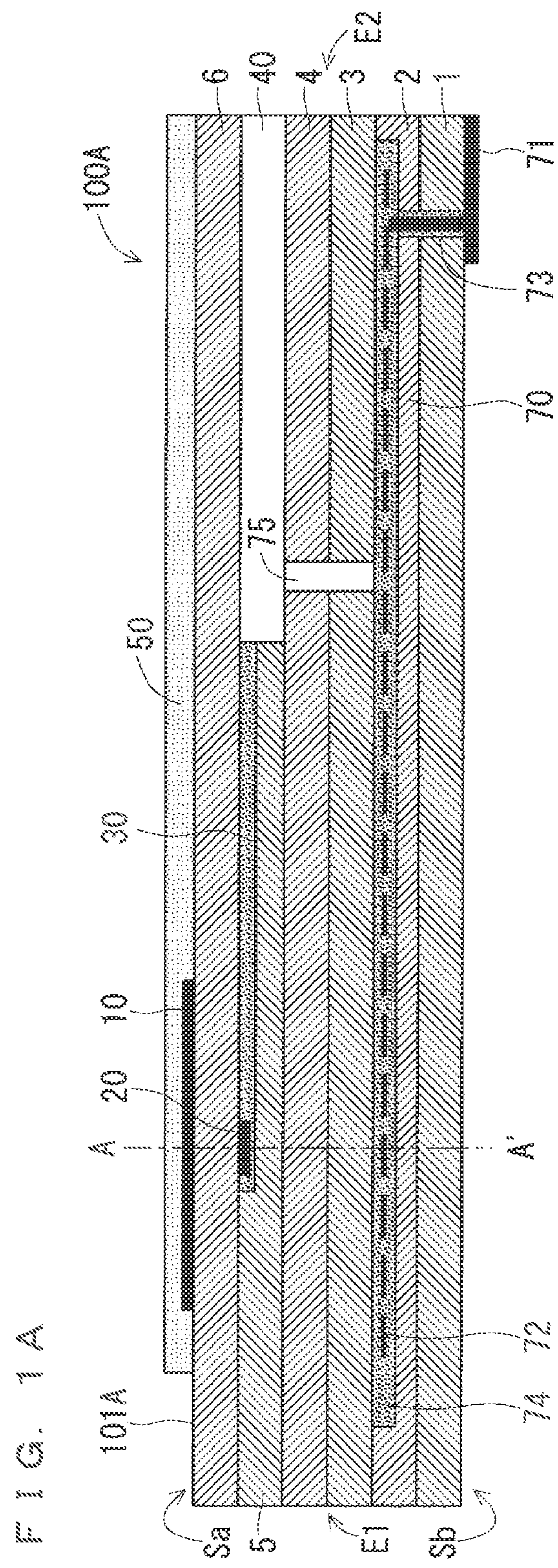
FIGS. 1A and 1B are sectional pattern diagrams each schematically illustrating a configuration of a gas sensor 100A.
Figure 1B:
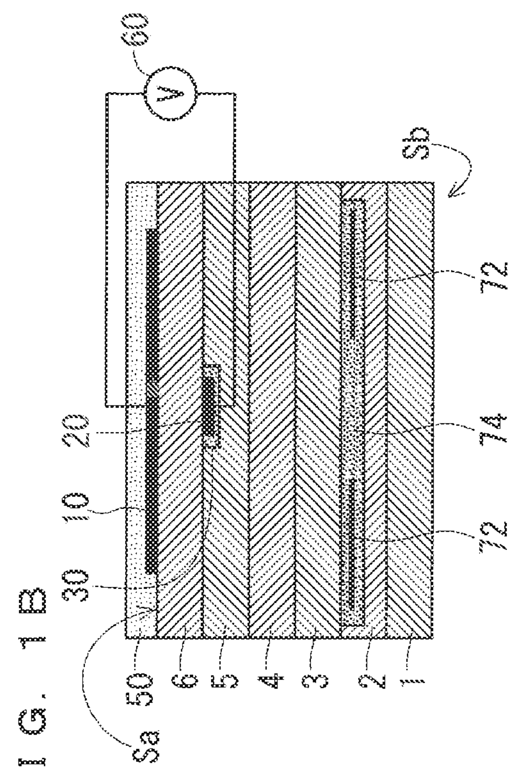

FIGS. 1A and 1B are sectional pattern diagrams each schematically illustrating a configuration of a gas sensor 100A as an exemplary inspection target in an inspection method according to the present preferred embodiment. FIG. 1A is a vertical sectional view of a sensor element 101A, which is a main component of the gas sensor 100A, taken along the longitudinal direction of the sensor element 101A. FIG. 1B is a diagram illustrating a section of the sensor element 101A taken along line A-A' in FIG. 1A perpendicular to the longitudinal direction of the sensor element 101A. The inspection method according to the present preferred embodiment generally relates to an inspection performed on a sensing electrode 10 provided on a surface of the sensor element 101A in the manufacturing process of the gas sensor 100A.

The gas sensor 100A is what is called a mixed-potential type gas sensor. Generally, the gas sensor 100A determines the concentration of a gas component as a measurement target in measurement gas by utilizing a potential difference generated between the sensing electrode 10 provided on the surface of the sensor element 101A mainly made of ceramic as oxygen-ion conductive solid electrolyte such as zirconia ($ZrO_2$) and a reference electrode 20 provided inside the sensor element 101A, the potential difference being attributable to the difference between the concentrations of the gas component near the both electrodes based on the principle of mixed potential.

More specifically, the gas sensor 100A preferably determines the concentration of a predetermined gas component in measurement gas that is exhaust gas present in an exhaust pipe of an internal combustion engine such as a diesel engine or a gasoline engine. Examples of gas components as measurement targets include hydrocarbon gas such as $C_2H_4$, $C_3H_6$, or n-C8, carbon monoxide (CO), ammonia ($NH_3$), steam ($H_2O$), nitrogen monoxide (NO), and nitrogen dioxide ($NO_2$). However, in the present specification, the hydrocarbon gas also includes carbon monoxide (CO) in some cases.

When a plurality of kinds of gas components are contained in measurement gas, the potential difference generated between the sensing electrode 10 and the reference electrode 20 has a value including contributions from all of the plurality of kinds of gas components in principle. However, in the same combinations of the contained gas components, the concentration values of individual kinds of gas can be individually obtained by preferably setting the drive temperature of the sensor element 101A and adjusting the properties (such as porosity and pore size) of a surface protective layer 50 to be described later. Alternatively, as for hydrocarbon gas, the concentrations of a plurality of kinds of hydrocarbon gas can be directly calculated in some cases. Certainly, it is acceptable that the gas sensor 100A is used under the condition that a gas component contained in measurement gas is limited to a particular gas component in advance and the concentration of the gas component is obtained.

In addition to the sensing electrode 10 and the reference electrode 20 described above, the sensor element 101A mainly includes a reference gas introduction layer 30, a reference gas introduction space 40, and the surface protective layer 50.

The sensor element 101A has a structure in which six layers, i.e., a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6 each made of oxygen-ion conductive solid electrolyte are stacked in this order from the bottom in FIGS. 1A and 1B. The sensor element 101A additionally includes other components mainly between the layers or on an outer peripheral surface of the element. The solid electrolyte of which the six layers are made is fully airtight.

However, it is not essential that the gas sensor 100A include the sensor element 101A as such a six-layer laminated body. The sensor element 101A may be formed as a laminated body having a larger or smaller number of layers or may not have a laminated structure.

In the following description, for sake of convenience, a surface located above the sixth solid electrolyte layer 6 in FIGS. 1A and 1B is referred to as a front surface Sa of the sensor element 101A, and a surface located below the first solid electrolyte layer 1 in FIGS. 1A and 1B is referred to as a rear surface Sb of the sensor element 101A. When the concentration of a predetermined gas component in measurement gas is obtained by using the gas sensor 100A, a predetermined range extending from a distal end E1 at one end of the sensor element 101A and including at least the sensing electrode 10 is disposed in a measurement gas atmosphere, while the other portion including a base end E2 at the other end is disposed avoiding contact with the measurement gas atmosphere.

The sensing electrode 10 is an electrode for sensing measurement gas. The sensing electrode 10 is formed as a porous cermet electrode made of Pt containing Au at a predetermined ratio, in other words, a Pt—Au alloy, and zirconia. The sensing electrode 10 is provided in a substantially rectangular shape in plan view at a position closer to the distal end E1 that is one end in the longitudinal direction on the front surface Sa of the sensor element 101A. When the gas sensor 100A is used, a portion of the sensor element 101A extending at least to a portion in which the sensing electrode 10 is provided is exposed to measurement gas.

The catalytic activity of the sensing electrode 10 against a measurement gas component in measurement gas is disabled in a predetermined concentration range by preferably determining the composition of the Pt—Au alloy which constitutes the sensing electrode 10. In other words, the combustion reaction of a measurement target gas component at the sensing electrode 10 is prevented or reduced. Accordingly, in the gas sensor 100A, the potential of the sensing electrode 10 selectively varies in accordance with (has correlation with) the concentration of a measurement target gas component through electrochemical reaction. In other words, the potential of the sensing electrode 10 has characteristics of high concentration dependency on a measurement target gas component in a predetermined concentration range and low concentration dependency on any other component in measurement gas.

More specifically, in the sensor element 101A of the gas sensor 100A according to the present preferred embodiment, Au is concentrated on the surface of a Pt—Au alloy particle forming the sensing electrode 10. In other words, an Au abundance ratio, which is the area ratio of a portion covered by Au to a portion at which Pt is exposed on the surface of a noble metal (Pt—Au alloy) particle forming the sensing electrode 10, is increased. Accordingly, the potential of the sensing electrode 10 exhibits significant dependency on the concentration of a measurement target gas component in a predetermined concentration range.

As disclosed in Japanese Patent Application Laid-Open No. 2016-33510, the Au abundance ratio can be calculated from peak intensities of Au and Pt at detection peaks, which can be obtained by X-ray photoelectron spectroscopy (XPS), by using a relative sensitivity coefficient method. Alternatively, as disclosed in Japanese Patent No. 5918434, the Au abundance ratio can be calculated by using detected values of Au and Pt in an Auger spectrum, which can be calculated by performing Auger electron spectroscopy (AES) analysis on a surface of a noble metal particle.

The Au abundance ratio increases as the degree of concentration of Au (Au maldistribution degree) on the surface of a noble metal particle of the sensing electrode 10 increases.

A high Au maldistribution degree at the sensing electrode 10 means that the concentration of Au on the surface (Au surface concentration) of a noble metal particle of the sensing electrode 10 is high. The Au abundance ratio indicates the ratio of an area of a portion covered by Au to an area of a portion at which Pt is exposed on the surface of a noble metal particle, whereas the Au surface concentration corresponds to the ratio of an area of a portion at which Au is exposed to an area of a whole surface of a noble metal particle. In place of or together with calculation of the Au abundance ratio, the Au surface concentration can be calculated by using a result of the XPS (X-ray photoelectron spectroscopy) analysis or the AES (Auger electron spectroscopy) analysis described above for calculation of the Au abundance ratio. In addition, the Au abundance ratio and the Au surface concentration have a mutually convertible relation. This is because, when $S_{Au}$ and $S_{Pt}$ represent the areas of portions at which Au and Pt, respectively, are exposed on a surface of a noble metal particle, the Au abundance ratio is given by $S_{Au}/S_{Pt}$, and the Au surface concentration (%) is given by $100\times S_{Au}/(S_{Au}+S^{Pt})$.

For example, when the area of the portion at which Pt is exposed is equal to the area of the portion covered by Au, in other words, when $S_{Au}=S_{Pt}$, the Au abundance ratio is one, and the Au surface concentration is 50%.

Thus, when a threshold is appropriately set, the Au surface concentration can be used as an index of the Au maldistribution degree in place of the Au abundance ratio.

The reference electrode 20 has a substantially rectangular shape in plan view and is provided inside the sensor element 101A and serves as a reference when the concentration of measurement gas is obtained. The reference electrode 20 is formed as a porous cermet electrode made of Pt and zirconia.

The reference electrode 20 is enough to be formed to have a porosity of 10% or more and 30% or less and a thickness of 5 μm or more and 15 μm or less. As illustrated in FIGS. 1A and 1B, the reference electrode 20 may have a plane size smaller than or equal to that of the sensing electrode 10.

The reference gas introduction layer 30 is made of porous alumina and provided to cover the reference electrode 20 inside the sensor element 101A. The reference gas introduction space 40 is an internal space provided near the base end E2 of the sensor element 101A. Air (oxygen), serving as a reference gas in the determination of the concentration of an inspection target gas component, is externally introduced to the reference gas introduction space 40.

The reference gas introduction space 40 and the reference gas introduction layer 30 are communicated with each other, so that the surrounding of the reference electrode 20 is constantly filled with air (oxygen) through the reference gas introduction space 40 and the reference gas introduction layer 30 when the gas sensor 100A is used. Thus, during the use of the gas sensor 100A, the reference electrode 20 always has a constant potential.

The reference gas introduction space 40 and the reference gas introduction layer 30 are prevented from contacting with measurement gas by the surrounding solid electrolyte. Thus, the reference electrode 20 does not come into contact with the measurement gas even when the sensing electrode 10 is exposed to the measurement gas.

In the configuration illustrated in FIG. 1A, the reference gas introduction space 40 is provided in a manner that a part of the fifth solid electrolyte layer 5 is communicated with the outside on the base end E2 side of the sensor element 101A. The reference gas introduction layer 30 is provided between the fifth solid electrolyte layer 5 and the sixth solid electrolyte layer 6 so as to extend in the longitudinal direction of the sensor element 101A. The reference electrode 20 is provided at a position below the center of gravity of the sensing electrode 10 in FIGS. 1A and 1B.

The surface protective layer 50 is a porous layer made of alumina and covering at least the sensing electrode 10 on the front surface Sa of the sensor element 101A. The surface protective layer 50 is provided as an electrode protective layer that prevents or reduces degradation of the sensing electrode 10 due to continuous exposure to measurement gas when the gas sensor 100A is used. In the configuration illustrated in FIG. 1A, the surface protective layer 50 covers not only the sensing electrode 10 but also a substantially entire portion of the front surface Sa of the sensor element 101A except for a predetermined range from the distal end E1.

As illustrated in FIG. 1B, the gas sensor 100A is provided with a potentiometer 60 capable of measuring the potential difference between the sensing electrode 10 and the reference electrode 20. FIG. 1B schematically illustrates wiring between the potentiometer 60 and each of the sensing electrode 10 and the reference electrode 20. However, in the actual sensor element 101A, a connection terminal (not illustrated) corresponding to each electrode is provided on the front surface Sa or the rear surface Sb on the base end E2 side, and a wiring pattern (not illustrated) connecting each electrode and the corresponding connection terminal is formed on the front surface Sa and inside the element. The sensing electrode 10 and the reference electrode 20 are each electrically connected with the potentiometer 60 through the wiring pattern and the connection terminal. Hereinafter, the potential difference between the sensing electrode 10 and the reference electrode 20, which is measured by the potentiometer 60 is also referred to as a sensor output.

The sensor element 101A further includes a heater part 70 configured to perform temperature adjustment involving heating and temperature maintenance of the sensor element 101A to increase the oxygen-ion conductivity of the solid electrolyte. The heater part 70 includes a heater electrode 71, a heater 72, a through-hole 73, a heater insulating layer 74, and a pressure diffusion hole 75.

The heater electrode 71 is formed in contact with the rear surface Sb of the sensor element 101A (a lower surface of the first solid electrolyte layer 1 in FIGS. 1A and 1B). Power can be supplied to the heater part 70 from the outside when the heater electrode 71 is connected with an external power source (not illustrated).

The heater 72 is an electric resistor provided inside the sensor element 101A. The heater 72 is connected with the heater electrode 71 through the through-hole 73, and generates heat with being powered externally through the heater electrode 71 to perform heating and temperature maintenance of the solid electrolyte forming the sensor element 101A.

In the configuration illustrated in FIGS. 1A and 1B, the heater 72 is buried while being vertically sandwiched between the second solid electrolyte layer 2 and the third solid electrolyte layer 3 in a range extending from the base end E2 to a position below the sensing electrode 10 near the distal end E1. With this configuration, the entire sensor element 101A can be adjusted to a temperature at which the solid electrolyte is activated.

The heater insulating layer 74 is made of insulator such as alumina and formed on upper and lower surfaces of the heater 72. The heater insulating layer 74 is formed to provide electric insulation between the second solid electrolyte layer 2 and the heater 72 and electric insulation between the third solid electrolyte layer 3 and the heater 72.

The pressure diffusion hole 75 is a site penetrating through the third solid electrolyte layer 3 and the fourth solid electrolyte layer 4 and communicated with the reference gas introduction space 40. The pressure diffusion hole 75 is formed to reduce increase in internal pressure along with increase in temperature inside the heater insulating layer 74.

When the concentration of a target gas component included in measurement gas is obtained by using the gas sensor 100A having the above-described configuration, only the predetermined range of the sensor element 101A extending from the distal end E1 and including at least the sensing electrode 10 is disposed in a space in which the measurement gas is present as described above, while the base end E2 side is isolated from the space to supply air (oxygen) into the reference gas introduction space 40. The heater 72 heats the sensor element 101A to an appropriate temperature of 400° C. to 800° C., preferably 500° C. to 700° C., more preferably 500° C. to 600° C. The temperature at which the heater 72 heats the sensor element 101A is also referred to as a sensor drive temperature.

In this state, a potential difference is generated between the sensing electrode 10 exposed to the measurement gas and the reference electrode 20 disposed in the air. However, as described above, the potential of the sensing electrode 10 selectively has concentration dependency on an inspection target gas component in the measurement gas whereas the potential of the reference electrode 20 being disposed in an air (with constant oxygen concentration) atmosphere is maintained constant. Thus, the potential difference (sensor output) substantially has a value in accordance with the composition of the measurement gas present in the surrounding of the sensing electrode 10. Accordingly, a constant functional relation (referred to as a sensitivity characteristic) holds between the concentration of the inspection target gas component and the sensor output. Hereinafter, such a sensitivity characteristic is also referred to as the sensitivity characteristic of the sensing electrode 10.

When actually obtaining the concentration of an inspection target gas component, the sensitivity characteristic is experimentally specified in advance by measuring the sensor output for each measurement gas of a plurality of mutually different mixed gases, in which the concentration of each inspection target gas component is known. Accordingly, when the gas sensor 100A is actually used, the sensor output, which momentarily changes in accordance with the concentration of an inspection target gas component in measurement gas, is converted into the concentration of the inspection target gas component based on the sensitivity characteristic by an arithmetic processing unit (not illustrated). In this manner, the concentration of the inspection target gas component in the measurement gas can be obtained substantially in real time.

<Manufacturing Process of Sensor Element>

The sensor element 101A having the layer structure as illustrated in FIGS. 1A and 1B can be manufactured through manufacturing processes disclosed in, for example, Japanese Patent Application Laid-Open No. 2016-33510 and Japanese Patent No. 5918434.

Generally, the sensor element 101A having the above-described configuration is manufactured as follows. First, predetermined processing, printing of circuit patterns for electrodes, and the like are performed on a plurality of ceramic green sheets containing oxygen-ion conductive solid electrolyte (for example, yttrium partially stabilized zirconia (YSZ)) as a ceramic component and corresponding to the respective solid electrolyte layers. Thereafter, the ceramic green sheets are laminated in a predetermined order, and a laminated body thus obtained is cut into units of elements to obtain a plurality of element bodies. Then, the element bodies are simultaneously fired to achieve integration of each element body, thereby simultaneously manufacturing a plurality of sensor elements 101A.

FIG. 2 is a diagram illustrating the flow of processing of manufacturing the sensor element 101A, which is showed for the purpose of confirmation. When the sensor element 101A is manufactured, first, a blank sheet (not illustrated), which is a green sheet on which no pattern is formed, is prepared (step S1). Specifically, six blank sheets corresponding to the first solid electrolyte layer 1 to the sixth solid electrolyte layer 6 are prepared. Each blank sheet is provided with a plurality of sheet holes used for positioning at printing and laminating. The sheet holes are formed in advance through, for example, punching processing by a punching device. Green sheets corresponding to layers forming an internal space also include penetrating portions corresponding to the internal space in advance through, for example, the punching processing as described above. Not all blank sheets corresponding to the respective layers of the sensor element 101A need to have equal thicknesses.

After the blank sheets corresponding to the respective layers are prepared, pattern printing and dry processing are performed to form various kinds of patterns on each blank sheet (step S2). Specifically, for example, a pattern of each electrode, a pattern of the heater 72, and an internal wire (not illustrated) are formed. In addition, a pattern of the surface protective layer 50 may be printed.

The printing of each pattern is performed by applying, to a blank sheet, pattern formation paste prepared in accordance with a characteristic requested for each formation target by using a well-known screen printing technique. Well-known drying means can be used for the dry processing after the printing.

After the pattern printing is completed, printing of bonding paste and dry processing are performed (step S3). The bonding paste is used to laminate and bond the green sheets corresponding to the respective layers to each other. A well-known screen printing technique can be used for the printing of the bonding paste, and well-known dry means can be used for the dry processing after the printing.

Subsequently, crimping processing is performed (step S4). In the crimping processing, the green sheets to which an adhesive has been applied are stacked in a predetermined order, and the stacked green sheets are crimped under predetermined temperature and pressure conditions to thereby form a laminated body. Specifically, crimping is performed by stacking and holding the green sheets as a target of lamination in a predetermined lamination jig (not illustrated) while positioning the green sheets at the sheet holes, and then heating and pressurizing the green sheets together with the lamination jig using a lamination machine, such as a known hydraulic pressing machine. The pressure, temperature, and time for heating and pressurizing depend on a lamination machine to be used, and these conditions may be set appropriately to achieve good lamination. The surface protective layer 50 may be formed on the laminated body as obtained.

After the laminated body is obtained as described above, the laminated body is cut out at a plurality of positions to obtain a plurality of element bodies (step S5). The cut out element bodies are fired under predetermined conditions, thereby producing the sensor elements 101A as described above (step S6). This means that the sensor element 101A is produced by integral firing (co-firing) of the solid electrolyte layers and the electrodes. The firing temperature is preferably 1,200° C. or higher and 1,500° C. or lower (e.g., 1,400° C.). Integral firing performed in such a manner provides sufficient adhesion strength to each of the electrodes of the sensor element 101A. This contributes to improvement in durability of the sensor element 101A.

The sensor element 101A obtained in this manner is subjected to various kinds of inspection processes such as a characteristic inspection, an appearance inspection, and a strength inspection. Only the sensor element 101A having passed all inspection processes is housed in a predetermined housing and incorporated in a main body (not illustrated) of the gas sensor 100A.

The pattern formation paste (conductive paste) used to form the sensing electrode 10 can be produced by preparing an Au ion-containing liquid as an Au starting material and mixing the Au ion-containing liquid with powdered Pt, powdered zirconia, and a binder. Any binder may be appropriately selected, as long as it can disperse any other raw material to an extent appropriate for printing and is burned out by firing.

The Au ion-containing liquid is obtained by dissolving a salt containing an Au ion or an organometallic complex containing an Au ion in a solvent. The Au ion-containing salt may be, for example, tetrachloroauric(III) acid ($HAuCl_4$), sodium chloroaurate(III) ($NaAuCl_4$), or potassium dicyanoaurate(I) ($KAu(CN)_2$). The Au ion-containing organometallic complex may be, for example, gold(III) diethylenediamine trichloride ($[Au(en)_2]Cl_3$), gold(III) dichloro(1,10-phenanthroline)chloride ($[Au(phen)Cl_2]Cl$), dimethyl (trifluoroacetylacetonate)gold, or dimethyl (hexafluoroacetylacetonate)gold. Tetrachloroauric(III) acid or gold(III) diethylenediamine chloride ($[Au(en)_2]Cl_3$) is preferably used from the viewpoint of no impurity such as Na or K remaining in the electrode, easy handling, or dissolvability in the solvent. The solvent may be acetone, acetonitrile, or formamide as well as alcohols such as methanol, ethanol, and propanol.

Mixing can be performed by well-known means such as instillation. Although the obtained conductive paste contains Au present in ionic (complex ionic) state, the sensing electrode 10 formed in the sensor element 101A obtained through the above-mentioned manufacturing process contain Au mainly as an elemental substrate or an alloy with Pt.

Alternatively, the conductive paste for the sensing electrode 10 may be prepared by using coated powder, which is obtained by coating powdered Pt with Au, as an Au starting raw material, instead of preparing the paste through liquid-state Au mixing as described above. In such a case, a conductive paste for the outer pump electrode is prepared by mixing the coated powder, zirconia powder, and a binder. Here, the coated powder may be obtained by covering the particle surface of powdered Pt with an Au film or applying Au particles to Pt powder particles.

<Inspection of Au Maldistribution Degree of Sensing Electrode>

The following describes inspection of the Au maldistribution degree at the sensing electrode 10 provided on the surface of the sensor element 101A of the gas sensor 100A manufactured through the above-described manufacturing process. The inspection is performed as one of the above-described various kinds of inspection processes.

As described above, a plurality of sensor elements 101A are manufactured at once by simultaneously firing a plurality of element bodies cut out from one laminated body. Thus, a plurality of sensor elements 101A obtained from one laminated body or a plurality of sensor elements 101A obtained by firing, under an identical condition, a plurality of element bodies obtained from a plurality of laminated bodies manufactured under an identical manufacturing condition are required to ideally have identical characteristics. Any variance in the characteristics is required to be within the range of a predetermined standard (inspection standard).

The same applies to the Au maldistribution degree of the sensing electrode 10, which largely affects the sensitivity characteristic of the sensor element 101A. Thus, at industrial mass production of the sensor element 101A, the Au maldistribution degree at the sensing electrode 10 of each sensor element 101A is required to be within the range of a predetermined standard (inspection standard).

As described above, direct evaluation of the Au maldistribution degree need to be performed based on the Au abundance ratio or the Au surface concentration calculated from results of analysis by XPS or AES. However, as a matter of course, the sensor element 101A cannot be inspected in a destructive manner in a mass production process. Meanwhile, a non-destructive inspection is limited to a case in which the sensor element 101A does not include the surface protective layer 50 or a case in which the surface protective layer 50 is formed after inspection, which is not a versatile method.

In the inspection method according to the present preferred embodiment, in place of direct evaluation of the Au maldistribution degree at the sensing electrode 10 based on an XPS or AES measurement result, the Au maldistribution degree is evaluated by using, as an alternative evaluation index (alternative maldistribution degree index) of the Au maldistribution degree, a physical property value correlated with the Au maldistribution degree. Specifically, the evaluation is performed in two aspects exemplarily described below with different physical property values actually used as the alternative maldistribution degree index.

(First Aspect: Evaluation Based on Reaction Resistance)

In the present aspect, reaction resistance (electrode reaction resistance) between the sensing electrode 10 and the reference electrode 20, which is correlated with the Au abundance ratio or the Au surface concentration is used as the alternative maldistribution degree index in the manufacturing process (mass production process) of the sensor element 101A. Hereinafter, the reaction resistance between the sensing electrode 10 and the reference electrode 20 of the sensor element 101A is also simply referred to as the reaction resistance of the sensor element 101A.

The reaction resistance of the sensor element 101A is obtained from plotting of a result of two-terminal complex impedance measurement in a Nyquist diagram having the real axis (Z' axis in units of Ω) as the horizontal axis and the imaginary axis (Z" axis in units of Ω) as the vertical axis. The two-terminal complex impedance measurement is performed by applying alternating-current voltage at different frequencies between the sensing electrode 10 and the reference electrode 20. FIGS. 3A to 3D are schematic Nyquist diagrams for description of derivation of the reaction resistance of the sensor element 101A.

Figure 3A:
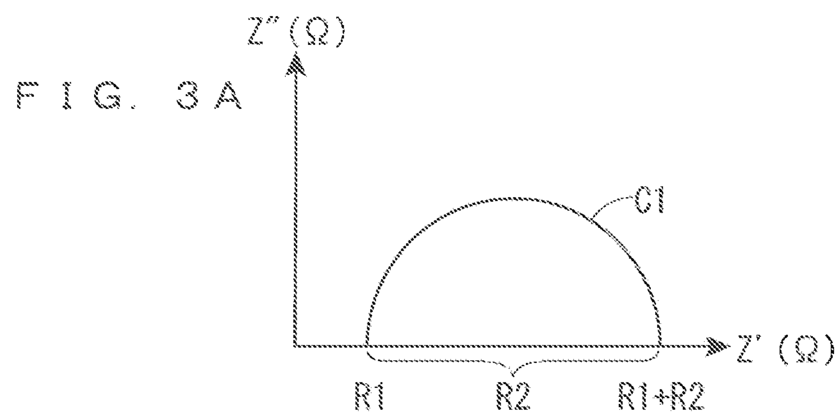
FIGS. 3A to 3D are schematic Nyquist diagrams for description of derivation of the reaction resistance of the sensor element 101A.
Figure 3B:
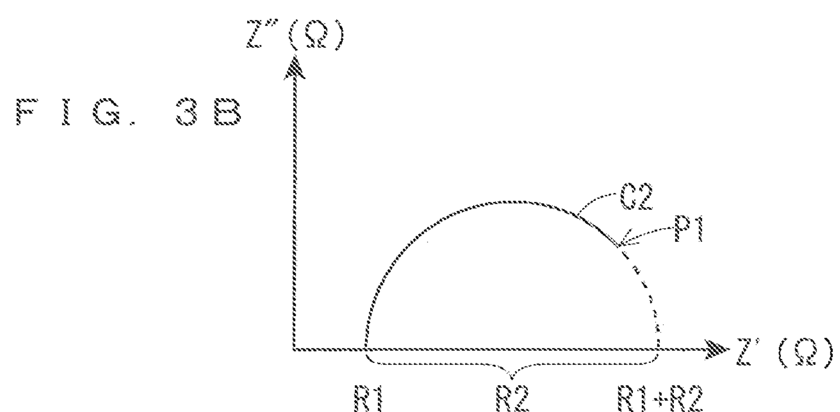
Figure 3C:
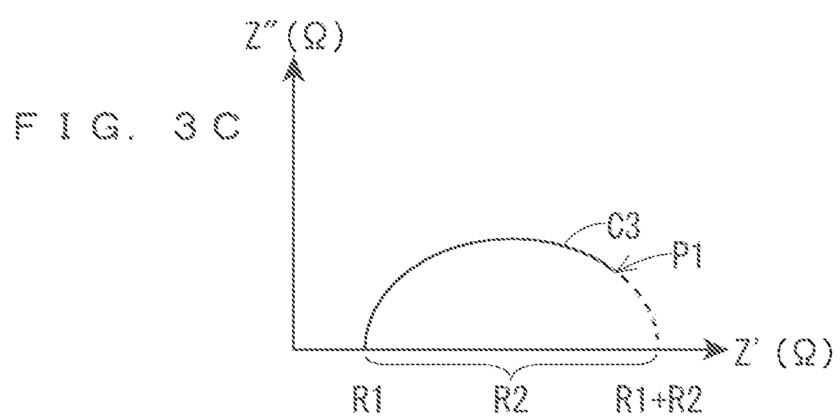

Plotting of measured data obtained by the two-terminal complex impedance measurement described above ideally obtains a semicircular curved line C1 starting at a point (Z', Z")=(R1, 0) on the real axis as illustrated in FIG. 3A. When the Z' coordinate value of an end point opposite to (Z', Z")=(R1, 0) on the curved line C1 is expressed as R1+R2, the reaction resistance is an increased value R2 of the Z' coordinate value from R1. The value R1 is an IR resistance (insulation resistance), and corresponds to, for example, the material resistance of a solid electrolyte forming a sensor element in a mixed-potential gas sensor such as the gas sensor 100A. Thus, the value of R1, not R2, varies when anomaly occurs in the solid electrolyte.

However, the plotting of measured data of the two-terminal complex impedance measurement does not necessarily draw a semicircle like the curved line C1 illustrated in FIG. 3A. For example, a result of the plotting obtains a semicircular curved line C2 illustrated in FIG. 3B, which starts at an end point (Z', Z")=(R1, 0) while the other end point does not reach the real axis Z' but ends at a halfway point P1, or another result of the plotting obtains a curved line C3 illustrated in FIG. 3C, which is not in a semicircular shape but in an arc shape ending at the halfway point P1.

In these cases, the reaction resistance R2 can be determined by using the Z' coordinate value of a point of extrapolation from the point P1 to the real axis Z'.

Figure 3D:
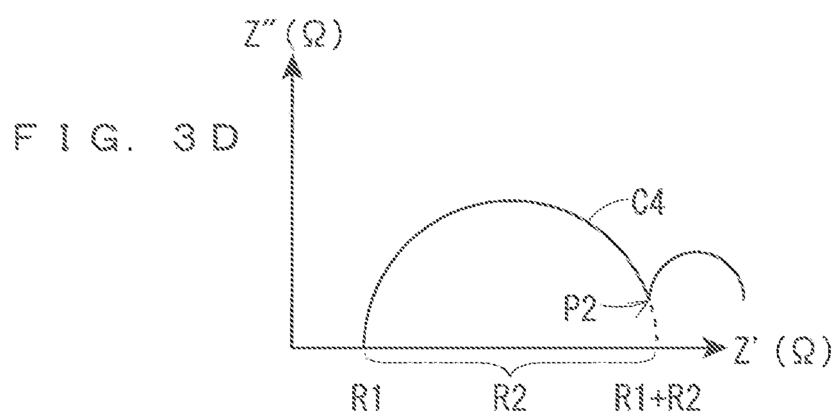

Another result of the plotting obtains two arcs connected with each other at a point P2 like a curved line C4 illustrated in FIG. 3D. In such a case, the arc formed in a range in which the Z' axis coordinate value is larger than that of the point P2 is reflected on diffusion resistance in the sensor element 101A. The reaction resistance can be obtained by extrapolation of the point P2, similarly to the cases in FIGS. 3B and 3C.

Figure 5:
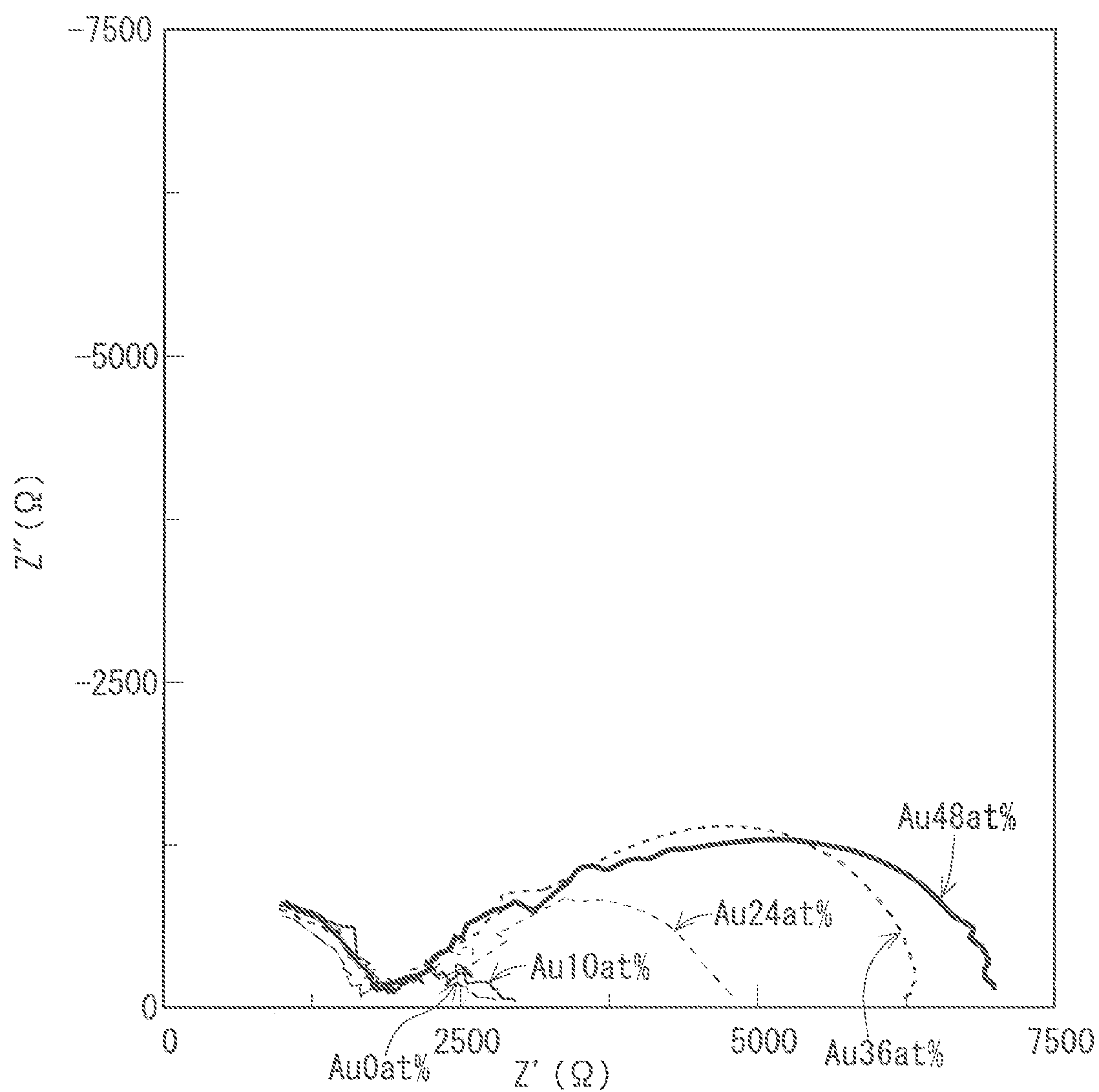
FIG. 5 is a Nyquist diagram illustrating a result of two-terminal complex impedance measurement performed at a sensor drive temperature of 750° C. to obtain the reaction resistances of the five sensor elements 101A having different Au maldistribution degrees at the sensing electrode 10.
Figure 6:
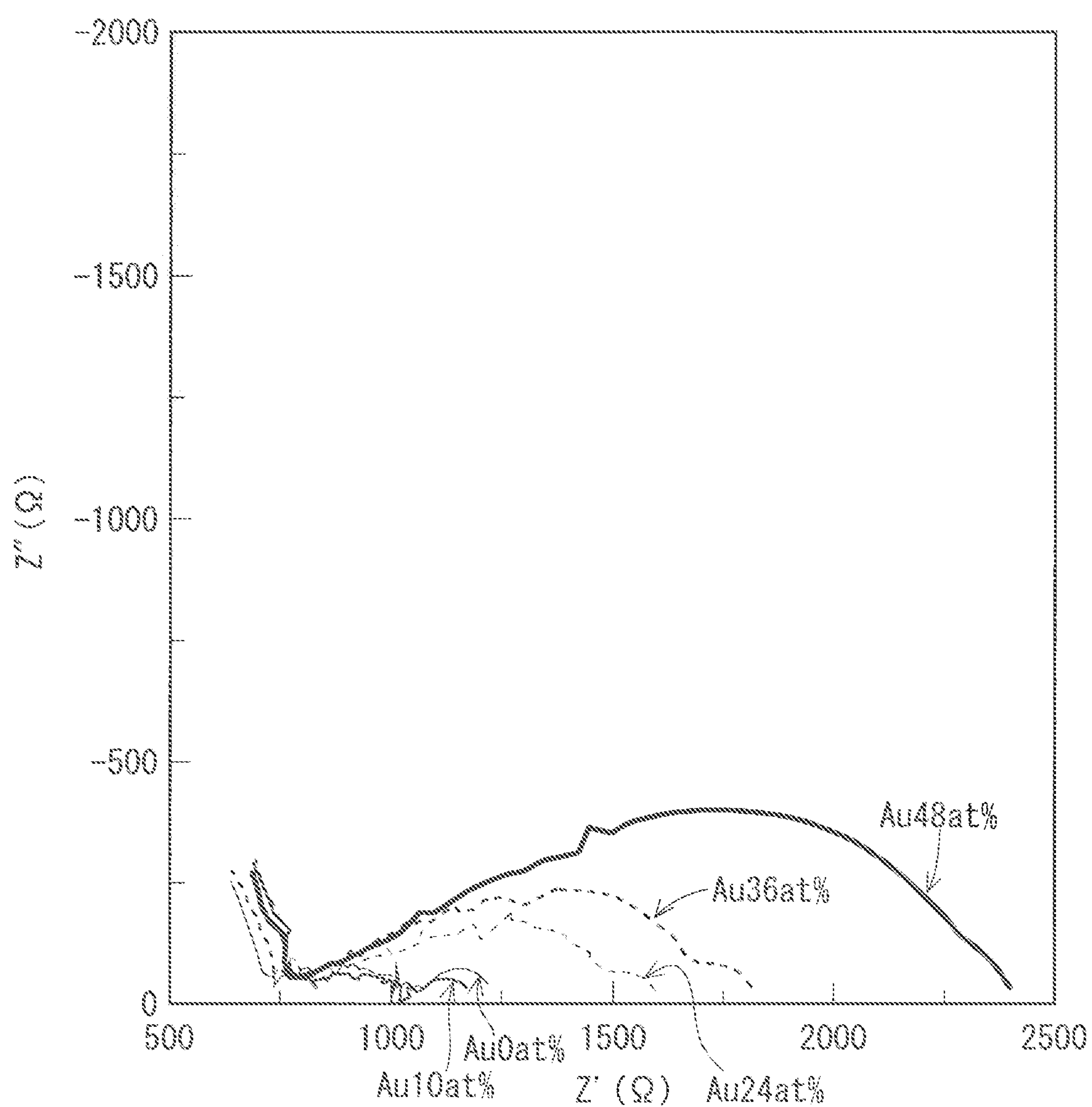
FIG. 6 is a Nyquist diagram illustrating a result of two-terminal complex impedance measurement performed at a sensor drive temperature of 850° C. to obtain the reaction resistances of the five sensor elements 101A having different Au maldistribution degrees at the sensing electrode 10.

FIGS. 4, 5, and 6 are Nyquist diagrams (Cole-Cole plots) illustrating results of the two-terminal complex impedance measurement performed to obtain the reaction resistance for five sensor elements 101A having different Au maldistribution degrees at the sensing electrode 10.

More specifically, the sensor drive temperature was set to three different levels of 640° C., 750° C., and 850° C. FIGS. 4, 5, and 6 illustrate results obtained when the sensor drive temperature was 640° C., 750° C., and 850° C., respectively. The surface protective layer 50 was not formed in any of the five sensor elements 101A to allow evaluation of the Au maldistribution degree based on XPS measurement. After the XPS measurement, the two-terminal complex impedance measurement was performed at each sensor drive temperature. The measurement was performed under air atmosphere by using a complex impedance measurement device Versa STAT 4 (manufactured by AMETEK Inc.), while the sensing electrode 10 was connected to a WE/SE line and the reference electrode 20 was connected to a CE/RE line. The frequency of alternating-current voltage was 1 MHz to 0.1 Hz, DC bias voltage was 0 V, and alternating-current amplitude was 20 mV.

Table 1 shows values of the Au surface concentration (in units of %), which are calculated based on results of the XPS measurement for the five sensor elements 101A, and the reaction resistance (in units of Ω) at each sensor drive temperature.

TABLE 1

| Au surface | Reaction resistance (Ω) | | |
|---|---|---|---|
| concentration (%) | 640° C. | 750° C. | 850° C. |
| 0 | 7219 | 1038 | 226 |
| 10 | 10486 | 1223 | 256 |
| 24 | 20897 | 3115 | 842 |
| 36 | 31459 | 4673 | 1068 |
| 48 | 40653 | 5388 | 1693 |

FIG. 7 is a diagram plotting, for each sensor drive temperature, the value of "reaction resistance/electrode area" (in units of $\Omega/mm^2$), which is a reaction resistance value per unit area of the sensing electrode 10, against the Au surface concentration. The value of "reaction resistance/electrode area" can be obtained by normalizing the values of the reaction resistance shown in Table 1 with the area of the sensing electrode.

FIG. 7 also illustrates, for the plotting result at each sensor drive temperature, an approximate straight line obtained by least square approximation when the Au surface concentration is taken to be x and the "reaction resistance/electrode area" is taken to be y. The function of each approximate straight line and a determination coefficient $R^2$ as the squared value of a correlation coefficient R are shown below. The area of the sensing electrode 10 is 0.4 $mm^2$.

$$640° \text{ C.}: y=1806.3x+17729, R^2=0.9859;$$

$$750° \text{ C.}: y=250.69x+1803, R^2=0.9684;$$

$$850° \text{ C.}: y=77.271x+218.5, R^2=0.9522.$$

As understood from FIG. 7 and the above-described values of the determination coefficient $R^2$, the (normalized) reaction resistance and the Au surface concentration have a linear relation (strong positive correlation) therebetween in any of the cases of 640° C., 750° C., and 850° C. The same result can be obtained at any other sensor drive temperature at least in the temperature range of 640° C. to 850° C. As a matter of course, when the reaction resistance and the Au surface concentration have a linear relation therebetween, the reaction resistance and the Au abundance ratio also have a linear relation therebetween. Although the reaction resistance value is normalized with the area of the sensing electrode 10 in the above description, a calibration curve may be produced based on the linear relation between the reaction resistance and the Au surface concentration or the Au abundance ratio without normalization because the area of the sensing electrode 10 is typically the same between the sensor elements 101A manufactured under the same condition.

In the present aspect, as the utilization of the fact that such a linear relation is established between the reaction resistance and the Au maldistribution degree at the sensing electrode 10, the Au maldistribution degree at the sensing electrode 10 of the sensor element 101A is inspected by using the reaction resistance as the alternative maldistribution degree index through an inspection process in the manufacturing process of the sensor element 101A.

To achieve this, such preparation is performed that the linear relation between the reaction resistance and the Au surface concentration or the Au abundance ratio, as illustrated in FIG. 7, for the sensor element 101A manufactured under a predetermined manufacturing condition is specified for a predetermined sensor drive temperature selected from, for example, the range of 640° C. to 850° C., and is recorded as a calibration curve in advance. This production of a calibration curve can be performed by manufacturing a plurality of sensor elements 101A all satisfying the same manufacturing condition except for different Au maldistribution degrees, performing the complex impedance measurement on the sensor elements 101A at a predetermined sensor drive temperature to measure the reaction resistances thereof, and then performing XPS or AES measurement to determine the Au surface concentration or the Au abundance ratio. When the surface protective layer 50 is provided, the sensing electrode 10 may be exposed by peeling the surface protective layer 50 or breaking the element before the XPS or AES measurement.

In an actual inspection process, the reaction resistance of the sensor element 101A manufactured under the same condition as the above predetermined manufacturing condition is measured while the sensor element 101A is driven at the same sensor drive temperature as that at which a calibration curve is produced, and the obtained measurement value is acquired as an inspection value. Then, the Au surface concentration or the Au abundance ratio is determined by comparing the inspection value with the calibration curve recorded in advance. When the Au surface concentration or the Au abundance ratio satisfies an inspection standard set in advance, it is determined that the sensor element 101A as an inspection target has passed the inspection.

A specific inspection standard for the Au surface concentration or the Au abundance ratio may be set in various manners based on, for example, a measurement target gas component and a measurement target concentration range (range in which highly sensitive measurement is desired) of the sensor element 101A as an inspection target. This is because, depending on the kind of gas, a concentration range in which highly sensitive measurement can be performed may differ depending on the Au maldistribution degree.

Alternatively, the range of the reaction resistance when the Au surface concentration or the Au abundance ratio satisfies an inspection standard set in advance may be specified in advance based on the linear relation between the reaction resistance and the Au surface concentration or the Au abundance ratio as illustrated in FIG. 7, and it may be determined that the sensor element 101A as an inspection target has passed the inspection when the measurement value (inspection value) of the reaction resistance belongs to the range.

(Second Aspect: Evaluation Based on Direct-Current Resistance)

The inspection according to the above-described first aspect needs to perform the complex impedance measurement at different frequencies to obtain the reaction resistance, and thus takes time. In the present aspect, to more easily perform inspection of the Au maldistribution degree at the sensing electrode 10 in a shorter time than in the first aspect, the direct-current resistance between the sensing electrode 10 and the reference electrode 20 is used as the alternative maldistribution degree index when the Au maldistribution degree is evaluated.

Figure 8:
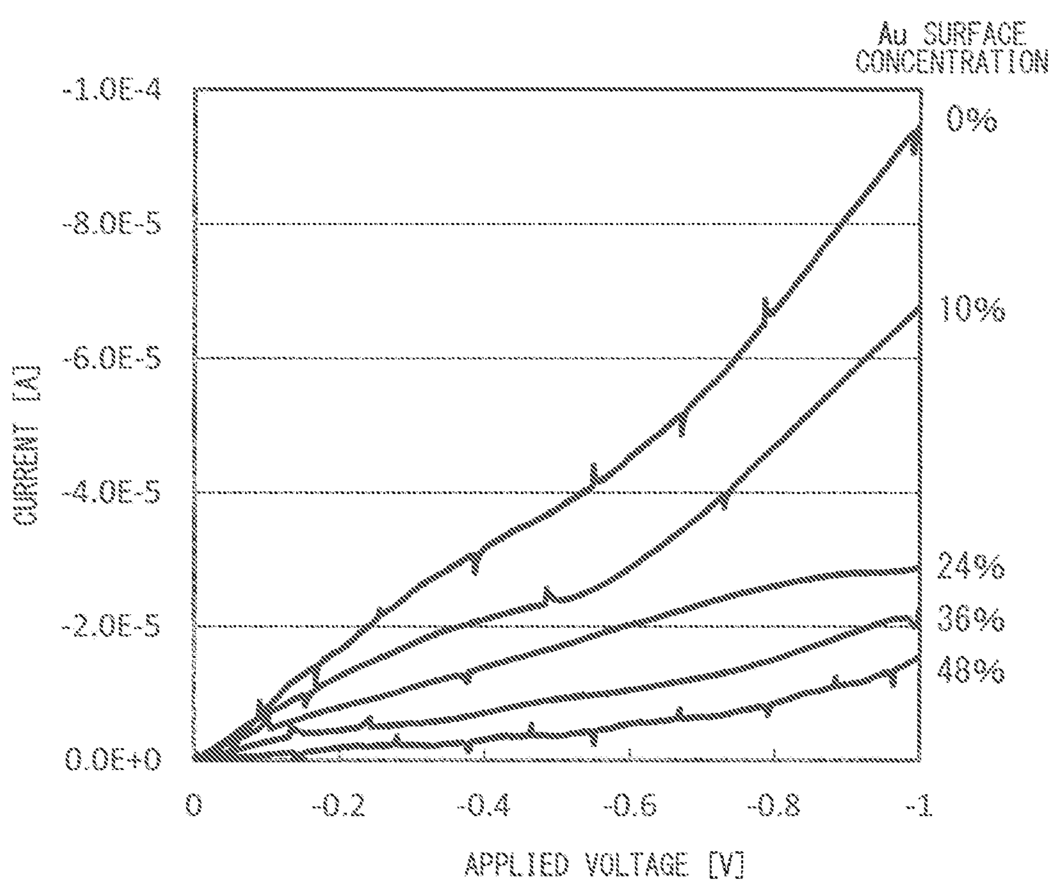
FIG. 8 is a diagram illustrating VI profiles of the five sensor elements 101A having different Au maldistribution degrees at the sensing electrode 10 when direct-current voltage is applied between the sensing electrode 10 and a reference electrode 20 at different voltage values at a sensor drive temperature of 640° C.

FIG. 8 is a diagram illustrating, for each of the five sensor elements 101A having different Au maldistribution degrees (different Au surface concentrations) at the sensing electrode 10, which are used to obtain the reaction resistance in the first aspect, a change (V-I profile) of a measurement value of current flowing between the sensing electrode 10 and the reference electrode 20 to the applied voltage value, in the case that direct-current voltage was applied at different voltage values while the sensor drive temperature was set to 640° C. Measurement was performed under air atmosphere by using the complex impedance measurement device Versa STAT 4 (manufactured by AMETEK Inc.) used in the complex impedance measurement in the first aspect, while the sensing electrode 10 was connected to a WE/SE line and the reference electrode 20 was connected to a CE/RE line. The applied voltage value was differed between 0 V to −1 V.

As understood from FIG. 8, the V-I profile differs in accordance with the Au maldistribution degree at the sensing electrode 10. Generally, at the same application voltage, the current value tends to be larger for the sensor element 101A having a smaller Au maldistribution degree.

Table 2 shows the Au surface concentration (in units of %), the (direct-current) current value (in units of A) when the applied voltage value is −1 V, and the (direct-current) resistance value (in units of Ω) for each of the five sensor elements 101A. The resistance value is obtained by dividing the applied voltage value (−1 V) by each current value.

TABLE 2

| Au surface concentration (%) | Current ($\times10^{-5}$ A) | Resistance (Ω) |
|---|---|---|
| 0 | −9.47 | 10560 |
| 10 | −6.77 | 14776 |
| 24 | −2.88 | 34678 |
| 36 | −2.27 | 44144 |
| 48 | −1.54 | 64934 |

FIG. 9 is a diagram plotting, against the Au surface concentration, the value of “resistance/electrode area” (in units of $\Omega/mm^2$), which is the value of direct-current resistance per unit area of the sensing electrode 10 and obtained by normalizing the resistance value shown in Table 2 with the area of the sensing electrode.

FIG. 9 also illustrates, for the plotting result, an approximate straight line calculated by least square approximation when the Au surface concentration is taken to be x and the “reaction resistance/electrode area” is taken to be y. The function of the approximate straight line and the determination coefficient $R^2$ as the squared value of the correlation coefficient R are shown below. The area of the sensing electrode 10 is 0.4 $mm^2$.

$$y=2842.5x+17464,\ R^2=0.974.$$

As understood from FIG. 9 and the above-described value of the determination coefficient $R^2$, the (normalized) direct-current resistance value and the Au surface concentration have a linear relation (strong positive correlation) therebetween. The same result can be obtained at any other sensor drive temperature at least in the temperature range of 640° C. to 850° C. As a matter of course, when the reaction resistance and the Au surface concentration have a linear relation therebetween, the reaction resistance and the Au abundance ratio also have a linear relation therebetween. Although the reaction resistance value is normalized with the area of the sensing electrode 10 in the above description, a calibration curve may be produced based on the linear relation between the reaction resistance and the Au surface concentration or the Au abundance ratio without normalization because the area of the sensing electrode 10 is typically the same between the sensor elements 101A manufactured under the same condition.

Thus, as the utilization the fact that such a linear relation is established, the Au maldistribution degree at the sensing electrode 10 of the sensor element 101A can be inspected by using the value of direct-current resistance between the sensing electrode 10 and the reference electrode 20 as the alternative maldistribution degree index.

To achieve this, such preparation is performed that the linear relation between the value of direct-current resistance between the sensing electrode 10 and the reference electrode 20 and the Au surface concentration or the Au abundance ratio, as illustrated in FIG. 9, for the sensor element 101A manufactured under a predetermined manufacturing condition is specified for a predetermined sensor drive temperature selected from, for example, the range of 640° C. to 850° C. and a predetermined direct-current voltage value, and is recorded as a calibration curve in advance. Specifically, this production of a calibration curve can be performed by manufacturing a plurality of sensor elements 101A all satisfying the same manufacturing condition except for different Au maldistribution degrees, measuring the direct current value by applying direct-current voltage at a predetermined voltage value (for example, −1 V) between the sensing electrode 10 and the reference electrode 20 of each sensor element 101A while being driven at a predetermined sensor drive temperature, thereby obtaining the direct-current resistance value, and then performing XPS or AES measurement to determine the Au surface concentration or the Au abundance ratio. Also in the present aspect, when the surface protective layer 50 is provided, the sensing electrode 10 may be exposed by peeling the surface protective layer 50 or breaking the element before the XPS or AES measurement.

In an actual inspection process, the value of direct current between the sensing electrode 10 and the reference electrode 20 in the sensor element 101A manufactured under a condition same as the above predetermined manufacturing condition is measured at a sensor drive temperature and a direct-current voltage value same as those at which a calibration curve is produced, and the value of direct-current resistance calculated from the obtained measurement value is acquired as an inspection value. Then, the Au surface concentration or the Au abundance ratio is determined by comparing the inspection value with the calibration curve recorded in advance. When the Au surface concentration or the Au abundance ratio satisfies an inspection standard set in advance, it is determined that the sensor element 101A as an inspection target has passed the inspection.

In this second aspect, measurement performed on the sensor elements 101A as individual inspection targets in the inspection process only involves single current measurement with application of a predetermined direct-current voltage value (for example, −1 V). Thus, in the second aspect, inspection can be performed faster than in the first aspect in which measurement needs to be repeated with different frequencies of alternating-current voltage to obtain the reaction resistance value.

Alternatively, since the linear relation between the value of direct-current resistance and the Au surface concentration or the Au abundance ratio as illustrated in FIG. 9 is obtained under a condition that the applied voltage value is constant, the range of the current value when the Au surface concentration or the Au abundance ratio satisfies an inspection standard set in advance may be specified in advance, and it may be determined that the sensor element 101A as an inspection target has passed inspection when a measured current value belongs to the range. In this case, the current value is an inspection value.

In any of the inspection methods according to the first and second aspects described above, the Au maldistribution degree at the sensing electrode 10 can be inspected without destructing the sensor elements 101A, except for that used to produce a calibration curve, by using the alternative maldistribution degree index correlated with the Au abundance ratio or the Au surface concentration, which indicates the Au maldistribution degree. Accordingly, it can be determined fast whether the Au maldistribution degree at the sensing electrode 10 satisfies a predetermined inspection standard as compared to a case in which XPS or AES analysis is performed to directly obtain the Au maldistribution degree. According to the present preferred embodiment, one-hundred percent inspection can be performed on the Au maldistribution degree at the sensing electrode 10 in the manufacturing process (mass production process) of the sensor elements 101A.

<Modifications>

The temperature range of 640° C. to 850° C. having upper and lower limit values at the temperatures of 640° C. and 850° C., which are used as the sensor drive temperature in the above-described preferred embodiment, covers the sensor drive temperatures of various kinds of sensor elements using solid electrolyte bodies, which are included in gas sensors of any other kinds such as a sensor element provided in a limiting-current gas sensor using an electrochemical pump cell, in addition to the sensor element of a mixed-potential gas sensor as described above. For example, the sensor drive temperature of a limiting-current NOx sensor is set to be 800° C. to 850° C. approximately. Thus, each inspection method according to the above-described preferred embodiment is applicable, not only to a sensor element provided in a mixed-potential gas sensor, but also to a sensor element containing solid electrolyte body as a main constituent material and including an electrode made of a Pt—Au alloy in which Au is concentrated on the surface of the noble metal particle.

While the invention has been shown and described in detail, the foregoing description is in all aspects illustrative and not restrictive. It is therefore understood that numerous modifications and variations can be devised without departing from the scope of the invention.

What is claimed is:

1. A method of inspecting an Au (Gold) maldistribution degree at a noble metal particle surface of an inspection target electrode, wherein said inspection target electrode is provided in a gas sensor element made of oxygen-ion conductive solid electrolyte, said inspection target electrode contains Pt (Platinum) and Au as noble metal components, said gas sensor element includes a heater inside, and said Au maldistribution degree is a value defined based on a ratio of an area of a portion at which Au is exposed on said noble metal particle surface, and calculated from a result of XPS (X-ray photoelectron spectroscopy) analysis or AES (Auger electron spectroscopy) analysis on said inspection target electrode, said method comprising the steps of:

a) producing, in advance, a calibration curve representing a relation between said Au maldistribution degree and a predetermined alternative maldistribution degree index correlated with said Au maldistribution degree and acquired in a non-destructive manner from said gas sensor element heated to a predetermined temperature by said heater;

b) acquiring, as an inspection value, a value of said alternative maldistribution degree index for said inspection target electrode of the gas sensor element as an inspection target while the gas sensor element is heated to said predetermined temperature; and c) determining whether the Au maldistribution degree at said inspection target electrode satisfies a predetermined standard based on said calibration curve produced through said step a) and said inspection value acquired through said step b).

2. The inspection method according to claim 1, wherein said alternative maldistribution degree index is reaction resistance between said inspection target electrode and a predetermined reference electrode provided in said gas sensor element, the reaction resistance being obtained by complex impedance measurement.

3. The inspection method according to claim 1, wherein said alternative maldistribution degree index is a value of direct-current resistance between said inspection target electrode and said reference electrode when predetermined direct-current voltage is applied between said inspection target electrode and a predetermined reference electrode provided in said gas sensor element.

4. The inspection method according to claim 1, wherein said alternative maldistribution degree index is a value of direct current flowing between said inspection target electrode and said reference electrode when predetermined direct-current voltage is applied between said inspection target electrode and a predetermined reference electrode provided in said gas sensor element.

5. The inspection method according to claim 1, wherein said Au maldistribution degree is defined by an Au surface concentration that is a ratio of an area of a portion at which said Au is exposed to an entire area of said noble metal particle surface.

6. The inspection method according to claim 1, wherein said Au maldistribution degree is defined by an Au abundance ratio that is a ratio of the area of a portion at which said Au is exposed to an area of a portion at which Pt is exposed on said noble metal particle surface.

7. The inspection method according to claim 1, wherein said predetermined temperature is 640° C. (Celsius) to 850° C.

8. The inspection method according to claim 1, wherein said gas sensor element is a mixed-potential gas sensor element, said inspection target electrode is a sensing electrode made of a cermet of Pt, Au, and zirconia and configured to sense a measurement target gas component in measurement gas, and said reference electrode is made of a cermet of Pt and zirconia.

9. The inspection method according to claim 2, wherein said Au maldistribution degree is defined by an Au surface concentration that is a ratio of an area of a portion at which said Au is exposed to an entire area of said noble metal particle surface.

10. The inspection method according to claim 2, wherein said Au maldistribution degree is defined by an Au abundance ratio that is a ratio of an area of a portion at which said Au is exposed to an area of a portion at which Pt is exposed on said noble metal particle surface.

11. The inspection method according to claim 2, wherein said predetermined temperature is 640° C. to 850° C.

12. The inspection method according to claim 2, wherein said gas sensor element is a mixed-potential gas sensor element, said inspection target electrode is a sensing electrode made of a cermet of Pt, Au, and zirconia and configured to sense a measurement target gas component in measurement gas, and said reference electrode is made of a cermet of Pt and zirconia.

13. The inspection method according to claim 3, wherein said Au maldistribution degree is defined by an Au surface concentration that is a ratio of an area of a portion at which said Au is exposed to an entire area of said noble metal particle surface.

14. The inspection method according to claim 3, wherein said Au maldistribution degree is defined by an Au abundance ratio that is a ratio of an area of a portion at which said Au is exposed to an area of a portion at which Pt is exposed on said noble metal particle surface.

15. The inspection method according to claim 3, wherein said predetermined temperature is 640° C. to 850° C.

16. The inspection method according to claim 3, wherein said gas sensor element is a mixed-potential gas sensor element, said inspection target electrode is a sensing electrode made of a cermet of Pt, Au, and zirconia and configured to sense a measurement target gas component in measurement gas, and said reference electrode is made of a cermet of Pt and zirconia.

17. The inspection method according to claim 4, wherein said Au maldistribution degree is defined by an Au surface concentration that is a ratio of an area of a portion at which said Au is exposed to an entire area of said noble metal particle surface.

18. The inspection method according to claim 4, wherein said Au maldistribution degree is defined by an Au abundance ratio that is a ratio of an area of a portion at which said Au is exposed to an area of a portion at which Pt is exposed on said noble metal particle surface.

19. The inspection method according to claim 4, wherein said predetermined temperature is 640° C. to 850° C.

20. The inspection method according to claim 4, wherein said gas sensor element is a mixed-potential gas sensor element, said inspection target electrode is a sensing electrode made of a cermet of Pt, Au, and zirconia and configured to sense a measurement target gas component in measurement gas, and said reference electrode is made of a cermet of Pt and zirconia.

* * * * *